(12) United States Patent
Kaufman et al.

(10) Patent No.: US 12,364,288 B2
(45) Date of Patent: Jul. 22, 2025

(54) APPARATUS FOR HEATING SMOKABLE MATERIAL AND ARTICLE OF SMOKABLE MATERIAL

(71) Applicant: British American Tobacco (Investments) Limited, London (GB)

(72) Inventors: Duane Anthony Kaufman, Hollandale, WI (US); Jesse Eugene Robinson, Janesville, WI (US)

(73) Assignee: British American Tobacco (Investments) Limited, London (GB)

( * ) Notice: Subject to any disclaimer, the term of this patent is extended or adjusted under 35 U.S.C. 154(b) by 48 days.

(21) Appl. No.: 18/320,471

(22) Filed: May 19, 2023

(65) Prior Publication Data

US 2023/0301362 A1    Sep. 28, 2023

Related U.S. Application Data

(63) Continuation of application No. 15/929,508, filed on May 6, 2020, now Pat. No. 11,849,769, which is a continuation of application No. 15/127,204, filed as application No. PCT/EP2015/055972 on Mar. 20, 2015, now Pat. No. 10,687,553.

(60) Provisional application No. 61/968,780, filed on Mar. 21, 2014.

(51) Int. Cl.
| | | |
|---|---|---|
| *A24F 47/00* | (2020.01) | |
| *A24B 15/16* | (2020.01) | |
| *A24B 15/167* | (2020.01) | |
| *A24F 40/50* | (2020.01) | |
| *A61M 15/06* | (2006.01) | |
| *G01D 5/24* | (2006.01) | |
| *A24F 40/20* | (2020.01) | |

(52) U.S. Cl.
CPC .............. *A24F 40/50* (2020.01); *A24B 15/16* (2013.01); *A24B 15/167* (2016.11); *A61M 15/06* (2013.01); *G01D 5/24* (2013.01); *A24F 40/20* (2020.01)

(58) Field of Classification Search
CPC ................. A24F 40/50; A24F 40/51
See application file for complete search history.

(56) References Cited

U.S. PATENT DOCUMENTS

| | | | | |
|---|---|---|---|---|
| 5,194,890 A | * | 3/1993 | Haruna ................... | G03B 27/32 355/77 |
| 5,303,579 A | * | 4/1994 | Smith, Jr. .............. | B65G 15/00 73/73 |
| 2010/0163063 A1 | * | 7/2010 | Fernando ................. | A24F 40/85 131/184.1 |
| 2014/0150810 A1 | * | 6/2014 | Hon ......................... | A24F 40/51 131/329 |

(Continued)

*Primary Examiner* — Eric Yaary
(74) *Attorney, Agent, or Firm* — BURR & FORMAN LLP (57) ABSTRACT

An apparatus is provided for enabling smokable material to be heated to volatize at least one component of the smokable material. In one example, the apparatus has a capacitive sensor arranged to sense a change in capacitance when an article of smokable material is associated with a housing of the apparatus in use. In another example, the apparatus has a resistive sensor arranged to provide a measure of electrical resistance when an article of smokable material is associated with a housing of the apparatus in use. A combination of capacitive and resistive sensing may be used in some examples. In another example, a sensor makes use of at least two different sensing techniques.

9 Claims, 9 Drawing Sheets

(56) References Cited

U.S. PATENT DOCUMENTS

2014/0299141 A1* 10/2014 Flick .................... H05B 1/0202
219/494
2014/0345633 A1* 11/2014 Talon ...................... A24F 40/53
702/30

* cited by examiner

APPARATUS FOR HEATING SMOKABLE MATERIAL AND ARTICLE OF SMOKABLE MATERIAL

CROSS REFERENCE TO RELATED APPLICATIONS

This application is a continuation of application Ser. No. 15/929,508 filed on May 6, 2020, which is a continuation of application Ser. No. 15/127,204 filed Sep. 19, 2016, now U.S. Pat. No. 10,687,553, which in turn is a National Phase Application of PCT/EP2015/055972, filed on Mar. 20, 2015, which claims the benefit of U.S. Provisional Patent Application No. 61/968,780, filed on Mar. 21, 2014, the entire contents of which are incorporated herein by reference.

TECHNICAL FIELD

The present disclosure relates to apparatus arranged to heat smokable material and to an article of smokable material.

BACKGROUND

Smoking articles such as cigarettes, cigars and the like burn tobacco during use to create tobacco smoke. Attempts have been made to provide alternatives to these articles that burn tobacco by creating products that release compounds without burning. Examples of such products are so-called heat-not-burn products which release compounds by heating, but not burning, the material. The material may be for example tobacco or other non-tobacco products, which may or may not contain nicotine.

SUMMARY

According to a first aspect of the present disclosure, there is provided an apparatus for enabling smokable material to be heated to volatize at least one component of said smokable material, the apparatus comprising: a housing; and a capacitive sensor arranged to sense a change in capacitance when an article of smokable material has been introduced into the housing in use to enable the article of smokable material to be identified.

In an exemplary embodiment, the capacitive sensor comprises an electrode, the apparatus comprising a processor constructed and arranged to sense a change in the capacitance of the electrode and an article of smokable material introduced into the housing in use.

In an exemplary embodiment, the capacitive sensor comprises at least two electrodes, the apparatus comprising a processor constructed and arranged to sense a change in the capacitance of the at least two electrodes when an article of smokable material is introduced into the housing in use. In an exemplary embodiment, the at least two electrodes are arranged such that at least a portion of an article of smokable material introduced into the housing in use can be positioned between the at least two electrodes.

In an exemplary embodiment, the apparatus comprises circuitry constructed and arranged so that the apparatus is only operated to cause heating of an article of smokable material introduced into the housing in use if the change in the capacitance meets at least one predetermined criterion.

In an exemplary embodiment, the apparatus comprises circuitry constructed and arranged so as to alternate between apply a charging voltage to the capacitive sensor to charge the capacitive sensor to a relatively high voltage and allowing the capacitive sensor to discharge to a relatively low voltage, the circuitry being arranged so that the apparatus is only operated to cause heating of an article of smokable material introduced into the housing in use if the number of transitions between the relatively high voltage and the relatively low voltage on the capacitive sensor in a predetermined time period is less than a predetermined number. In an exemplary embodiment, the predetermined number is the number of transitions between the relatively high voltage and the relatively low voltage on the capacitive sensor in the predetermined time period when no article of smokable material is introduced into the housing.

In an exemplary embodiment, the apparatus comprises a resistive sensor arranged to provide a measure of electrical resistance when an article of smokable material is introduced into the housing in use.

In an exemplary embodiment, the apparatus comprises a heater operable to heat an article of smokable material received within the housing in use.

According to a second aspect of the present disclosure, there is provided an apparatus for enabling smokable material to be heated to volatize at least one component of said smokable material, the apparatus comprising: a housing; and a resistive sensor arranged to provide a measure of electrical resistance when an article of smokable material has been introduced into the housing in use to enable the article of smokable material to be identified.

In an exemplary embodiment, the resistive sensor comprises at least two electrodes, the apparatus comprising a processor constructed and arranged to provide a measure of electrical resistance using the at least two electrodes when an article of smokable material is introduced into the housing in use. In an exemplary embodiment, the at least two electrodes are arranged such that at least a portion of an article of smokable material introduced into the housing in use can be positioned between and in contact with the at least two electrodes, the at least two electrodes in use providing a measure of the electrical resistance of said at least a portion of an article of smokable material.

In an exemplary embodiment, the apparatus comprises circuitry constructed and arranged so that the apparatus is only operated to cause heating of an article of smokable material introduced into the housing in use if the electrical resistance meets at least one predetermined criterion.

In an exemplary embodiment, the apparatus comprises a heater operable to heat an article of smokable material received within the housing in use.

According to a third aspect of the present disclosure, there is provided an apparatus for enabling smokable material to be heated to volatize at least one component of said smokable material, the apparatus comprising: a housing; and a sensor arrangement constructed and arranged to identify an article of smokable material when associated with the housing in use by making use of at least two different sensing technique.

In an exemplary embodiment, one of the at least two different sensing techniques uses capacitive sensing and another of the at least two different sensing techniques uses resistive sensing.

In an exemplary embodiment, one of the at least two different sensing techniques uses electrical sensing and another of the at least two different sensing techniques uses optical sensing. Suitable optical sensing techniques include for example the use of and detection of bar codes (which may be the conventional linear type or the more recent two dimensional type), using for example some kind of optical emitter, such as one or more LEDs (light emitting diodes), laser or the like, and corresponding detector or detectors. Visible or non-visible light may be used, depending on for example the nature of the indicium or marker or the like in use on the smokable material.

In an exemplary embodiment, the apparatus comprises a heater operable to heat an article of smokable material received within the housing in use.

According to a fourth aspect of the present disclosure, there is provided an article of smokable material, the article having a non-metallic electrically conductive region for detection by a sensor of an apparatus arranged to cause heating of the smokable material.

In an exemplary embodiment, the non-metallic electrically conductive region is in the form of a band of material that at least partly encircles the article.

In an exemplary embodiment, the non-metallic electrically conductive region comprises carbon.

In an exemplary embodiment, the non-metallic electrically conductive region is a printed ink.

In some example embodiments, the smokable material article may be received (at least in part) within the housing. In such example embodiments, the apparatus may itself include a heater operable to heat the article of smokable material received within the housing in use. In some other example embodiments, the smokable material article may contain the smokable material, for example in liquid or other form, in combination with a heater. In such example embodiments, the smokable material article with integral heater may be connected to the apparatus in use, with the apparatus typically containing a power supply for the heater.

BRIEF DESCRIPTION OF THE DRAWINGS

Embodiments of the disclosure will now be described, by way of example only, with reference to the accompanying drawings, in which.

DETAILED DESCRIPTION

As used herein, the term "smokable material" includes materials that provide volatilized components upon heating, typically in the form of an aerosol. "Smokable material" includes any tobacco-containing material and may, for example, include one or more of tobacco, tobacco derivatives, expanded tobacco, reconstituted tobacco or tobacco substitutes. "Smokable material" also may include other, non-tobacco, products, which, depending on the product, may or may not contain nicotine.

Figure 1:
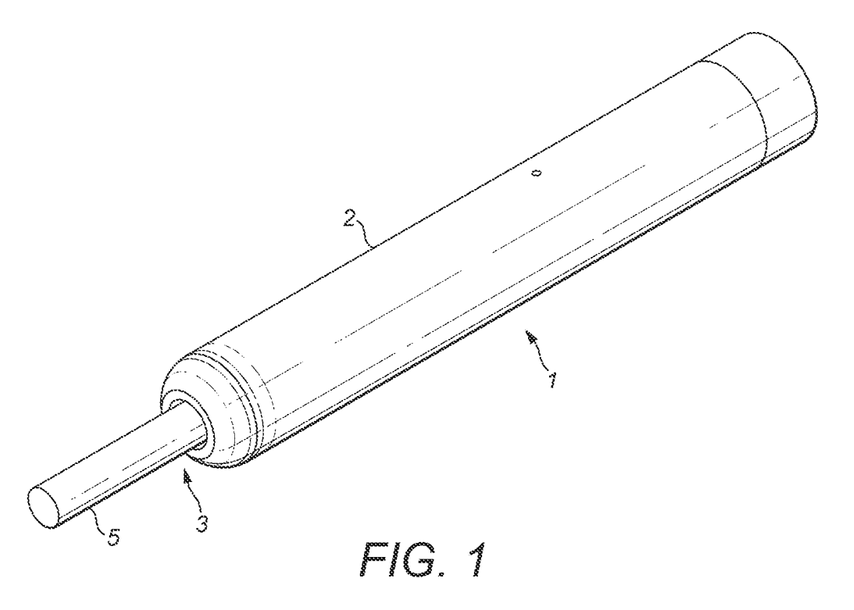
FIG. 1 shows a perspective view of an example of an apparatus for heating a smokable material.

Referring to FIG. 1, there is shown a perspective view of an example of an apparatus 1 arranged to heat smokable material to volatize at least one component of said smokable material, typically to form an aerosol which can be inhaled. The apparatus 1 is a so-called "heat-not-burn" apparatus 1. The apparatus 1 in this example is generally elongate, having a generally elongate cylindrical outer housing 2 of circular cross-section. The outer housing 2 has an open end 3, sometimes referred to herein as the mouth end. The outer housing 2 may be formed of a heat insulating material. A particularly suitable material is polyether ether ketone (PEEK), though other plastics, including for example acrylonitrile butadiene styrene (ABS), or other heat insulating materials, may be used. The outermost surface of the outer housing 2 may have a decorative coating, such as a metallic finish. The innermost surface of the outer housing 2 may be coated, partially or fully, with a material that is a good heat conductor. By way of example, a metal coating, such as of copper, may be used for this purpose.

Figure 2:
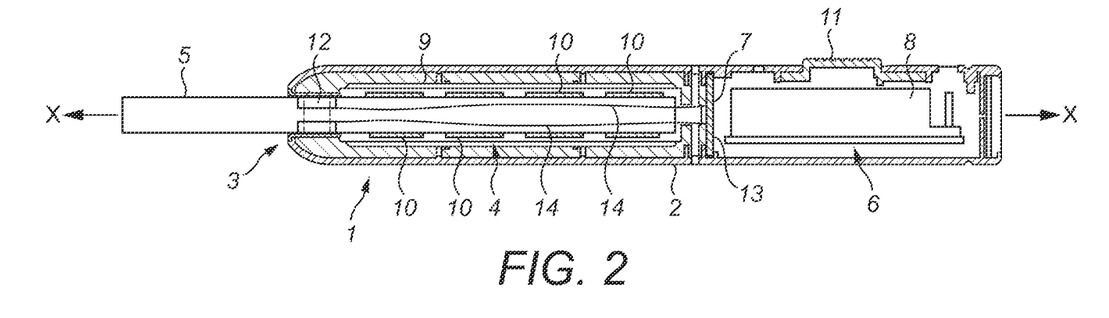
FIG. 2 shows a longitudinal cross-sectional view of an example of an apparatus for heating a smokable material.

FIG. 2 shows a cross-sectional view of an example of an apparatus 1 for heating a smokable material. The apparatus 1 has a heating chamber 4 which in use contains the smokable material to be heated and volatized. The smokable material may be in the form of an article 5, formed of or containing smokable material, which can be removably inserted into the apparatus 1 by a user. The smokable material article 5 may be a generally elongate cylinder, for example a cartridge or cassette or rod. The smokable material article 5 is in use inserted into the housing 2. An end of the smokable material article 5 projects out of the apparatus 1 through the open end 3 of the housing 2, typically for connection to a filter or the like, which may be a separate item or provided with the smokable material article 5, through which a user inhales in use.

The apparatus 1 further has an electronics/power chamber 6 which in this example contains electrical control circuitry 7 and a power source 8. In this example, the heating chamber 4 and the electronics/power chamber 6 are adjacent each other along the longitudinal axis X-X of the apparatus 1. In the example shown, the electronics/power chamber 6 is remote from the mouth end 3, though other locations are possible. The electrical control circuitry 7 may include a controller, such as a microprocessor arrangement, configured and arranged to control the heating of the smokable material and also to recognize or identify the smokable material article 5, as discussed further below. The electrical control circuitry 7 may in use receive a signal from for example a puff-actuated sensor which is sensitive to for example changes in pressure or changes in rate of air flow that occur upon initiation of a draw on the smokable material article 5 by a user. The electrical control circuitry 7 can then operate so as to cause heating of the smokable material article 5 "on demand" when required. Various arrangements for a puff-actuated sensor are available, including for example a thermistor, an electro-mechanical device, a mechanical device, an optical device, an opto-mechanical device and a micro electro mechanical systems (MEMS) based sensor. As an alternative, the apparatus may have a manually operable switch for a user to initiate a puff.

The power source 8 may be a battery, which may be a rechargeable battery or a non-rechargeable battery. Examples of suitable batteries include for example a lithium-ion battery, a nickel battery (such as a nickel-cadmium battery), an alkaline battery and/or the like. A particularly preferred type of battery is a $LiFePO_4$ battery. The battery 8 is electrically coupled to the one or more heating elements (to be discussed further below) of the heating chamber 4 to supply electrical power when required and under control of the electrical control circuitry 7 to heat the smokable material (as discussed, to volatize the smokable material without causing the smokable material to burn). In this example, the battery 8 is contained within a printed circuit board of the electrical control circuitry 7. In other examples, the battery 8 and the electrical control circuitry 7 may be arranged differently, such as for example arranged adjacent each other along the longitudinal axis X-X of the apparatus 1.

The heating chamber 4 is contained within a heater support sleeve 9, which is contained within the outer housing 2. In this example, the heater support sleeve 9 is a generally elongate cylinder of circular cross-section. In an example, the heater support sleeve 9 is a double-walled or "vacuum" sleeve, having an outer cylindrical wall and an inner cylindrical wall which are joined to each other at each end and separated by a small separation d. As just one example and to give an idea of scale, the heater support sleeve 9 may be around 50 mm long and have an outer diameter of around 9 mm, and the separation d may be around 0.1 mm to 0.12 mm or so. One of the functions of the heater support sleeve 9 in one example is to assist in heat-insulating the outer housing 2 from the heating chamber 4, so that the outer housing 2 does not become hot or at least too hot to touch during use. The space between the outer and inner cylindrical walls of the heater support sleeve 9 may contain air. However, the space between the outer and inner cylindrical walls of the heater support sleeve 9 is preferably evacuated to improve the heat insulating properties of the heater support sleeve 9. As an alternative, the space between the outer and inner cylindrical walls of the heater support sleeve 9 may be filled with some other insulating material, including a suitable foam-type material for example. The material of the heater support sleeve 9 is preferably such that the heater support sleeve 9 is rigid to provide structural stability for the components mounted therein. An example of a suitable material is stainless steel. Other suitable materials include polyether ether ketone (PEEK), ceramics, glass, steel, aluminum, etc.

In one example of the apparatus 1, the heater support sleeve 9 contains at least one heating element 10 and may contain plural heating elements or heater segments 10. There are preferably at least two heater segments 10, though arrangements with other numbers of heater segments 10 are possible. In the particular example shown, there are four heater segments 10. In this example, the heater segments 10 align along or parallel to the longitudinal axis X-X of the heater support sleeve 9. The electrical control circuitry 7 and the power connections to the heater segments 10 are preferably arranged such that at least two, and more preferably all, of the heater segments 10 can be powered independently of each other, so that selected zones of the smokable material article 5 can be independently heated, for example in turn (over time) or together (simultaneously) as desired. In this particular example, the heater segments 10 are generally annular or cylindrical, having a hollow interior which in use contains the smokable material article 5. In an example, the heater segments 10 may be made of a ceramics material. Examples include alumina and aluminum nitride and silicon nitride ceramics, which may be laminated and sintered. The apparatus 1 has an on/off switch 11 projecting through the outer housing 2 for operation by a user.

Different shapes and different configurations for the or each heater segment 10 may be used. Moreover, other heating arrangements are possible, including for example infrared heater segments 10, which heat by emitting infrared radiation, or resistive heating elements formed by for example a resistive electrical winding around the heater segments 10. Yet other different heating arrangements may be used.

It is sometimes desirable for the apparatus 1 to be able to identify or recognize the particular smokable material article 5 that has been introduced into the apparatus 1 by a user. For example, in practice, the apparatus 1 as a whole, including in particular the heating arrangement and the heating control provided by the electrical control circuitry 7, will often be optimized for a particular arrangement of the smokable material article 5 (e.g. one or more of size, shape, particular smokable material, etc.) and it would be undesirable for the apparatus 1 to be used with smokable material or a smokable material article 5 having (significantly) different characteristics. In addition, if the apparatus 1 can identify or recognize the particular smokable material article 5, or at least the general type of smokable material article 5, that has been introduced into the apparatus 1, this can help eliminate or at least reduce counterfeit or other non-genuine smokable material articles 5 being used with the apparatus 1. The apparatus 1 may be arranged so that it will only heat a smokable material article 5 that it recognizes, and will not operate in conjunction with a smokable material article 5 that it does not recognize. The apparatus 1 may be arranged so that it provides some indication to the user that the smokable material article 5 has not been recognized. This indication may be visual (for example a warning light, which may for example flash or be illuminated continuously for a period of time) and/or audible (for example a warning "beep" or the like). Alternatively or additionally, the apparatus 1 may be arranged so that for example it follows a first heating pattern when it recognizes a first type of smokable material article 5 and follows a second, different heating pattern when it recognizes a second type of smokable material article 5 (and optionally may provide yet further heating patterns for other types of smokable material article 5). The heating patterns may differ in a number of ways, for example the rate of delivery of heat to the smokable material, the timing of various heating cycles, which part(s) of the smokable material are heated first, etc. This enables the same apparatus 1 to be used with different basic types of smokable material article 5 with minimal interaction required of the user.

In an example of an embodiment, the apparatus 1 is constructed and arranged to use capacitive sensing to sense a change in capacitance when an article of smokable material 5 is received within the housing 2 in use. In another example of an embodiment, the apparatus 1 is constructed and arranged to use resistive sensing to sense a smokable material article 5 received within the housing 2. In another example of an embodiment, the apparatus 1 is constructed and arranged to use a combination of capacitive and resistive sensing to sense a smokable material article 5 received within the housing 2. In an example of an embodiment, the apparatus 1 senses a change in capacitance when a smokable material article 5 is received within the housing 2. The capacitance when a smokable material article 5 is received within the housing 2 may in effect be compared with the capacitance when a smokable material article 5 is not present within the housing 2. In any of these examples, this enables some identification or recognition of a particular smokable material article 5 received within the housing. In an example of an embodiment, a smokable material article 5 is provided so as to be able to be sensed by a sensor of an apparatus 1 as described herein. In a particular example of an embodiment, a smokable material article 5 is provided with a strip or band or other marker or indicium or indicia which can be sensed by a sensor of an apparatus 1 as described herein.

In general, capacitive sensing as used herein operates by effectively sensing a change in capacitance when the smokable material article 5 is located within the apparatus 1. In effect, in an embodiment, a measure of the capacitance is obtained. If the capacitance meets one or more criteria, it may be decided that the smokable material article 5 is suitable for use with the apparatus 1, which can then proceed to operate as normal to heat the smokable material. Otherwise, if the capacitance does not meet the one or more criteria, it may be decided that the smokable material article 5 is not suitable for use with the apparatus 1, and the apparatus 1 does not function to heat the smokable material and/or may issue some warning message to the user.

Figure 7:
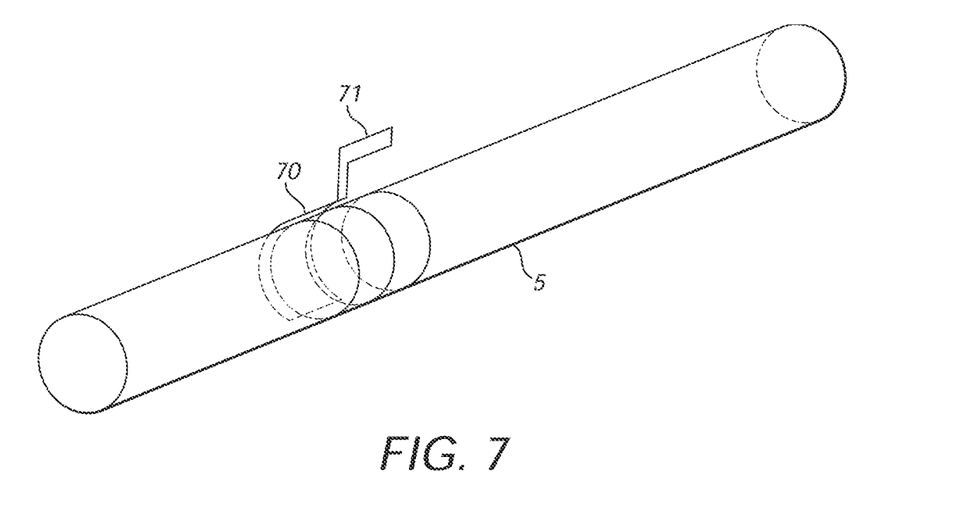
FIG. 7 shows a perspective view of an example of an electrode and a smokable material article.

In general, capacitive sensing as used herein may work in one of two ways. First, the apparatus 1 may be provided with (at least) one electrode which in effect provides one "plate" of a capacitor, with the other "plate" of the capacitor being provided by the smokable material article 5 (or at least by some feature on the smokable material article 5, such as the marker or indicium mentioned above and discussed further below). An example of this is shown schematically in FIG. 7, which shows a perspective view of just the electrode 70 and portions of a connecting wire 71 which connects to sensing circuitry in the apparatus 1, without the other parts of the apparatus 1 being illustrated in FIG. 7. When the smokable material article 5 is inserted into the apparatus 1, a measure of the capacitance formed by the combination of the electrode 70 of the apparatus 1 and the smokable material article 5 can be obtained, and then compared to one or more criteria to determine whether the apparatus 1 can then proceed to heat the smokable material.

As an alternative, the apparatus 1 may be provided with (at least) two electrodes, which in effect provide the pair of "plates" of a capacitor. When the smokable material article 5 is inserted into the apparatus 1, it is inserted between the two electrodes. As a result, the capacitance formed between the two electrodes of the apparatus 1 changes. A measure of this capacitance formed by the two electrodes of the apparatus 1 can be obtained, and then compared to one or more criteria to determine whether the apparatus 1 can then proceed to heat the smokable material.

Figure 3:
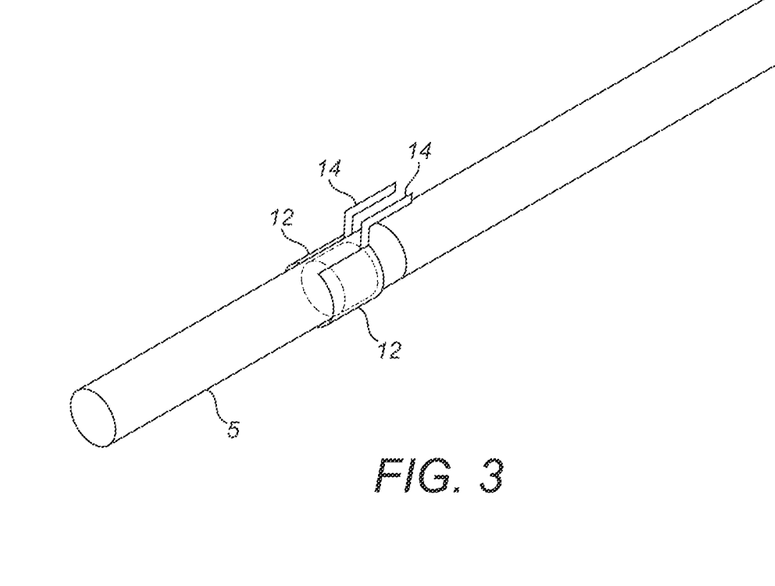
FIG. 3 shows a perspective view of an example of electrodes with a smokable material article inserted therebetween.
Figure 4:
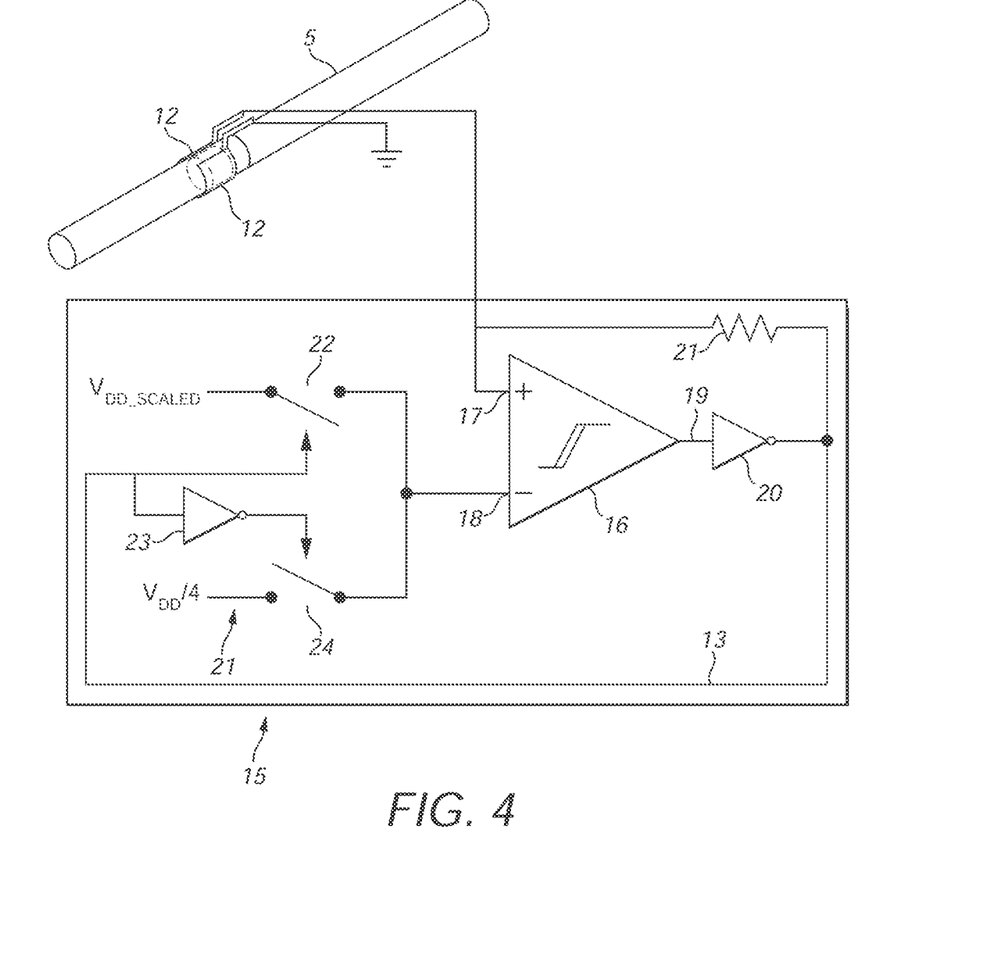
FIG. 4 shows schematically an example of connection of electrodes to sensing circuitry.

The example shown in FIG. 2 is an example of apparatus 1 that uses (at least) two electrodes to allow capacitive sensing to sense a smokable material article 5 received within the housing 2. In particular, in this example, the apparatus 1 has two electrodes 12 located near the open end 3 of the outer housing 2. The two electrodes 12 are curved, each electrode 12 being almost semi-circular in cross-section so as to define a generally circular opening into which the smokable material article 5 passes when received in the housing 2. In the example shown, the electrodes 12 extend somewhat longitudinally, generally parallel to the longitudinal axis of the apparatus 1, so as to create a larger area of overlap of the electrodes 12 and therefore increase the effective capacitance. The electrodes 12 are connected to sensing circuitry 13 via connecting wires 14. The sensing circuitry 13 may be provided as part of the electrical control circuitry 7, for example as part of the controller, such as the microprocessor, described above, or as separate circuitry. For the purposes of illustration, FIG. 3 shows a perspective view of just the electrodes 12 and portions of the connecting wires 14 (without the other parts of the apparatus 1) with a smokable material article 5 inserted therebetween. FIG. 4 shows schematically the connection of the electrodes 12 to the sensing circuitry 13. It is emphasized that the sensing circuitry 13 may be separate from or integrally formed with the electrical control circuitry 7, for example as part of the controller, such as the microprocessor, and indeed the function of the sensing circuitry 13 may be provided entirely by the controller, such as the microprocessor. An example of sensing circuitry 13 is shown schematically in FIG. 4, it being understood that other arrangements for the sensing circuitry 13 are possible, whether as part of the controller, such as the microprocessor, of the apparatus 1 or as separate circuitry.

In this example, the combination of the electrodes 12 and the sensing circuitry 13 provides a capacitive sensor 15. In this example, the sensing circuitry 13 alternates between supplying voltage to one of the capacitor electrodes 12 and allowing voltage to drain from the one of the capacitor electrodes 12. The other of the capacitor electrodes 12 is earthed (for example by being electrically connected to the outer housing 2 of the apparatus 1).

In more detail, in an example, the sensing circuitry 13 has an op-amp (operational amplifier) or other differential amplifier 16 having a non-inverting input 17 and an inverting input 18. An output 19 of the op-amp 16 is connected to an inverter 20. The non-inverting input 17 is connected to the one of the capacitor electrodes 12. The non-inverting input 17 is also connected via a resistor 21 to the output of the inverter 20. The output of the inverter 20 is also connected to a voltage control portion 21 of the sensing circuitry 13. The voltage control portion 21 passes the output of the inverter 20 to control a first switch 22 and, via a second inverter 23, to control a second switch 24. The outputs of the first and second switches 22,24 are connected to the inverting input 18 of the op-amp 16. The input of the first switch 22 is at a relatively high voltage $V_{DD\_SCALED}$ and the input of the second switch 24 is at a relatively low voltage $V_{DD}/4$.

In an example, the operation of this example of the apparatus 1 is as follows. First, when the apparatus 1 is in a state where there is no smokable material article 5 inserted in the apparatus 1, the apparatus 1 periodically makes a calibration of the capacitive sensor 15 provided by the combination of the sensing circuitry 13 and capacitor electrodes 12 to establish a baseline value, against which subsequent measurements will be assessed. In particular, advantageously under control of the controller of the electrical control circuitry 7 of the apparatus 1, a high "excitation" voltage is applied to the one of the electrodes 12. This causes the charge and therefore voltage on the one of the electrodes 12 to increase, the increase being at a characteristic rate defined by the resistance and capacitance present in the relevant parts of the capacitive sensor 15. This high "excitation" voltage is also applied to the voltage control portion 21, which causes the first switch 22 to close and the second switch 24 to open so that the input voltage $V_{DD\_SCALED}$ of the first switch 22 is applied to the inverting input 18 of the op-amp 16.

Once the voltage on the one of the electrodes 12, which is applied to the non-inverting input 17 of the op-amp 16, reaches a predetermined value (in this example, the input voltage $V_{DD\_SCALED}$ of the first switch 22), the output of the op-amp 16 switches. This causes the first switch 22 to open and the second switch 24 to close so that the input voltage $V_{DD}/4$ of the second switch 24 is applied to the inverting input 18 of the op-amp 16. At the same time, the charge on the one of the electrodes 12 drains through the resistor 21, causing the voltage on the one of the electrodes 12 to fall at a characteristic rate defined by the resistance and capacitance present in the relevant parts of the capacitive sensor 15. Once the voltage on the one of the electrodes 12 falls to a second predetermined value (in this example, the input voltage $V_{DD}/4$ of the second switch 24), the output of the op-amp 16 switches back again and the process is repeated.

Figure 5:
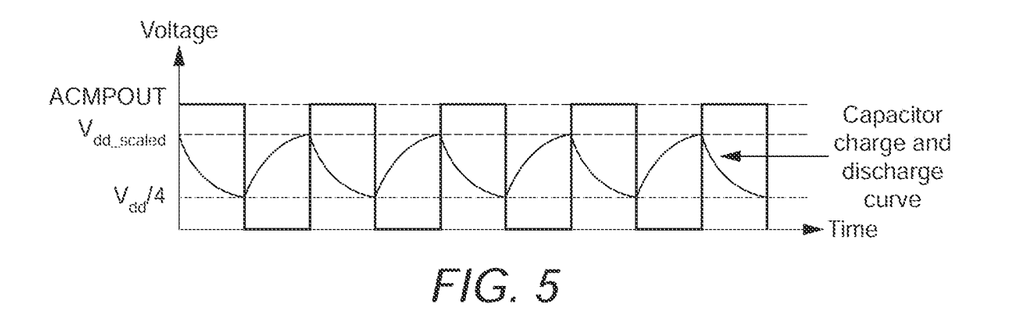
FIG. 5 shows an example of a graph of voltage versus time.

The effect of this can be seen in FIG. 5. FIG. 5 shows a graph of voltage vs. time. The bold lines show a square wave type voltage that alternates between applying a high voltage to the one of the electrodes 12 to charge the electrode 12 and removing that voltage to allow the charge on the one of the electrodes 12 to drain away. (In the example shown, when ACMPOUT is high, $V_{DD}/4$ is selected as the reference voltage, and, due to the inverter 20, the one of the electrodes 12 starts to discharge. When the capacitor voltage drops below $V_{DD}/4$, the ACMPOUT level toggles to a low state and $V_{DD\_SCALED}$ is selected as the reference and the charge on the one of the electrodes 12 starts to increase. When the capacitor voltage again reaches $V_{DD\_SCALED}$, the ACMPOUT toggles (goes high), $V_{DD}/4$ is again selected as a reference voltage, and the cycle repeats.) The alternating charging and discharging of the one of the electrodes 12 is indicated by a light grey line. It can be seen that the increase and then decay of the charge or voltage on the one of the electrodes 12 each takes place at a characteristic rate.

Then, upon user initiation, i.e. when the user has inserted a smokable material article 5 into the apparatus 1 and initiates a session (for example, by operating some actuator switch and/or by use of a puff-actuated sensor), the controller of the apparatus 1 reads the capacitive sensor 15 in a similar way. In particular, again, advantageously under control of the controller of the electrical control circuitry 7 of the apparatus 1, a high "excitation" voltage is applied to the one of the electrodes 12. This causes the charge and therefore voltage on the one of the electrodes 12 to increase, the increase being at a characteristic rate defined by the resistance and capacitance present in the relevant parts of the capacitive sensor 15. This high "excitation" voltage is also applied to the voltage control portion 21, which causes the first switch 22 to close and the second switch 24 to open so that the input voltage $V_{DD\_SCALED}$ of the first switch 22 is applied to the inverting input 18 of the op-amp 16. Once the voltage on the one of the electrodes 12, which is applied to the non-inverting input 17 of the op-amp 16, reaches a predetermined value (in this example, the input voltage $V_{DD\_SCALED}$ of the first switch 22), the output of the op-amp 16 switches. This causes the first switch 22 to open and the second switch 24 to close so that the input voltage $V_{DD}/4$ of the second switch 24 is applied to the inverting input 18 of the op-amp 16. At the same time, the charge on the one of the electrodes 12 drains through the resistor 21, causing the voltage on the one of the electrodes 12 to fall at a characteristic rate defined by the resistance and capacitance present in the relevant parts of the capacitive sensor 15. Once the voltage on the one of the electrodes 12 falls to a second predetermined value (in this example, the input voltage $V_{DD}/4$ of the second switch 24), the output of the op-amp 16 switches back again and the process is repeated.

Figure 6:
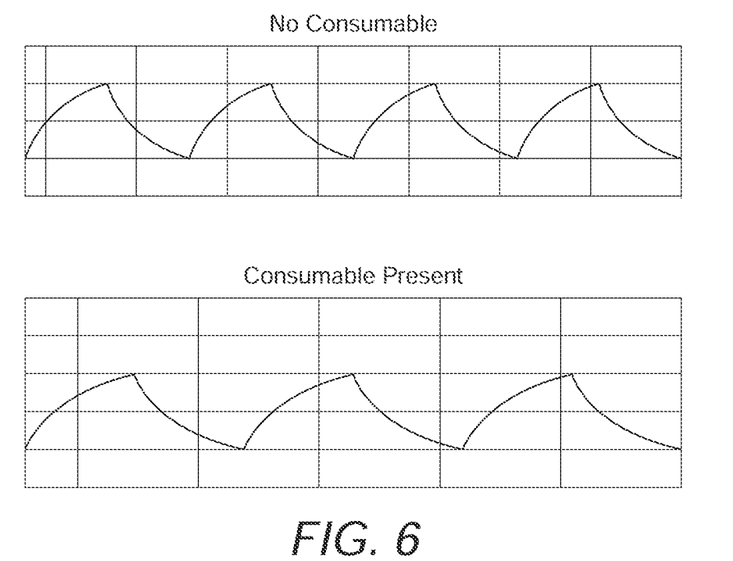
FIG. 6 shows an example of the change of detected voltage over time when no smokable material article is present and when a smokable material article is present.

In this case, because the smokable material article 5 is present between the electrodes 12, the capacitance of the capacitive sensor 15 is different. This means that the increase and decrease of voltage on the one of the electrodes 12 occurs at a different rate (and indeed with a different profile). This can be seen in FIG. 6, in which the upper trace shows the change of detected voltage on the one of the electrodes 12 when no smokable material article 5 is present (as in FIG. 5) and the lower trace shows the change of detected voltage on the one of the electrodes 12 when a smokable material article 5 is present between the electrodes 12. As can be seen, when a smokable material article 5 is present between the electrodes 12, in this case the capacitance is higher and so the rate of increase of voltage and likewise the rate of decrease of voltage is lower when smokable material article 5 is present between the electrodes 12.

This difference in capacitance when a smokable material article 5 is or is not present between the electrodes 12 can be detected in a number of different ways to determine whether a smokable material article 5 is present, and in particular whether a correct or appropriate smokable material article 5 is present. For example, the difference in the voltage trace, shown schematically in the upper and lower parts of FIG. 6, can be used to obtain a measure of the value of the capacitance when a smokable material article 5 is present between the electrodes 12. In another example, the controller of the electrical control circuitry 7 of the apparatus 1 counts how many transitions (from high voltage to low voltage say) occur in a given time period. Because the rates of charge and discharge are related to the capacitance present in the capacitive sensor 15, the number of transitions that occur in a given time are related to the capacitance present: a higher capacitance, such as when a smokable material article 5 is present, leads to fewer transitions in a given time period. The controller of the electrical control circuitry 7 of the apparatus 1 compares the number of transitions in a given time period with that obtained during the calibration process (i.e. when no smokable material article 5 was present). If the number of transitions over a certain time period is below some predetermined threshold, or falls within a predetermined range, then the smokable material article 5 is considered genuine, and the session is allowed to complete to result in the smokable material article 5 being heated. If however the number of transitions over a certain time period is above the predetermined threshold or does not fall within the predetermined range, then the smokable material article 5 is not considered genuine and a heating session will not start; optionally, the user can be notified separately, as mentioned above. As an alternative, rather than using an absolute threshold number for the number of transitions (from high voltage to low voltage say) say, the threshold number for the number of transitions when a smoking material article 5 is present in the apparatus 1 may be a certain proportion or percentage of the number of transitions when a smoking material article 5 is not present in the apparatus 1 (as in the calibration phase discussed above). It will be understood that the number of transitions between a maximum voltage and a minimum voltage on the capacitive sensor over a certain time period is a measure of the rate of charge/discharge of the capacitive sensor 15. In a specific example, and without limitation, some nominal values are $V_{DD\_SCALED}=2.25V$, $V_{DD}/4=0.56V$, the measurement time is 0.1 second, and the number transitions per measurement is 1000. In a specific actual example during testing, the number of transitions per measurement when no smoking material article 5 is present in the apparatus 1 was 1100 whereas the number of transitions per measurement when a smoking material article 5 is present in the apparatus 1 was 1050.

It may be noted that apparatus 1 that has (at least) two electrodes 12 for capacitive sensing of the smokable material article 5 may alternatively operate as described above where one electrode 12 in effect provides one "plate" of a capacitor, with the other "plate" of the capacitor being provided by the smokable material article 5 (or at least by some feature on the smokable material article 5, such as the marker or indicium mentioned above and discussed further below). (This is in contrast to the specific example described above where the capacitance between the two electrodes 12 is sensed.) When the smokable material article 5 is inserted into the apparatus 1, a measure of the capacitance formed by the combination of the electrode 12 of the apparatus 1 and the smokable material article 5 can be obtained, and then compared to one or more criteria to determine whether the apparatus 1 can then proceed to heat the smokable material. Having plural electrodes 12 spaced around the open end 3 of the apparatus 1 for this purpose is of advantage in that the orientation of the smokable material article 5 around the longitudinal axis X-X in the apparatus 1 is less important, as in general at least one of the electrodes 12 will be close enough to the smokable material article 5 sense the capacitance sufficiently.

In the specific example of FIGS. 2 to 4, the two electrodes 12 are generally or almost semi-circular and face each other on opposite sides of the outer housing 2 to define the generally circular opening into which the smokable material article 5 passes when received in the housing 2. Different shapes and arrangements for the electrodes 12 are possible.

Figure 8:
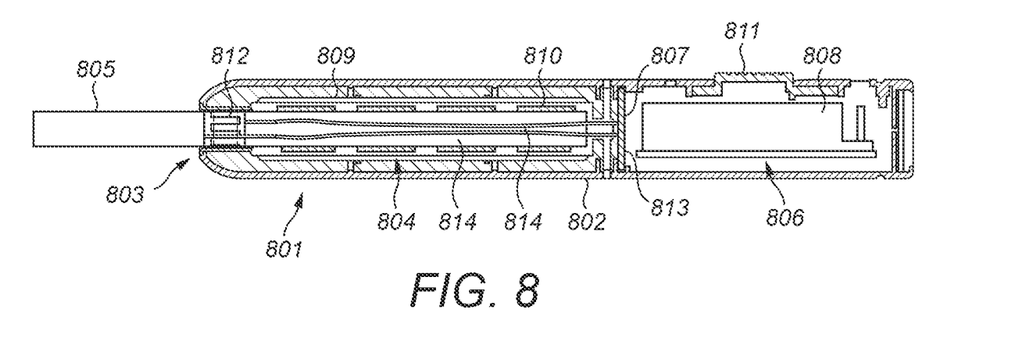
FIG. 8 shows a longitudinal cross-sectional view of another example of an apparatus for heating a smokable material.
Figure 9:
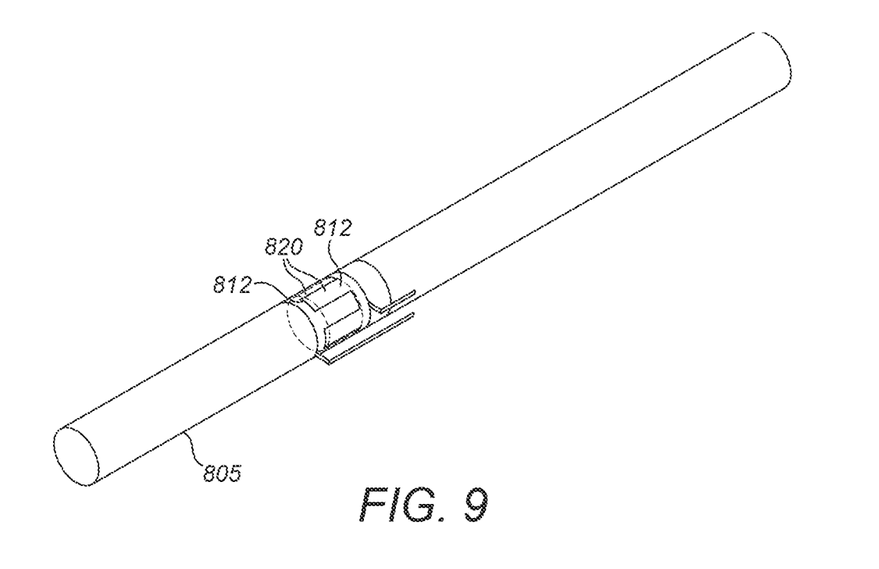
FIG. 9 shows a perspective view of another example of electrodes with a smokable material article inserted therebetween.

For example, FIGS. 8 and 9 show another example of apparatus 801 that uses (at least) two electrodes 812 located near the open end 803 of the outer housing 802 to allow capacitive sensing to sense a smokable material article 805 received within the housing 802.

Components and circuitry that are the same as or at least functionally similar to corresponding items in the example of FIGS. 2 and 3 have similar reference numerals, but increased by "800". Thus, the example apparatus 801 shown in FIGS. 8 and 9 has a heating chamber 804, an electronics/power chamber 806 containing electrical control circuitry 807 and a power source 808, a heater support sleeve 809, plural heating elements or heater segments 810, and an on/off switch 811, etc., all of which may be the same as or at least functionally similar to the corresponding components of the example shown schematically in FIGS. 2 to 4. Other heating arrangements are possible, including for example infrared heater segments 810, which heat by emitting infrared radiation, or resistive heating elements formed by for example a resistive electrical winding around the heater segments 810. Yet other different heating arrangements may be used.

In the example of FIGS. 8 and 9, the two electrodes 812 are interdigitated. As with the example of FIGS. 2 and 3, the electrodes 812 are connected to sensing circuitry 813 via connecting wires 814. The sensing circuitry 813 may be provided as part of the electrical control circuitry 807, for example as part of the controller, such as the microprocessor, described above, or as separate circuitry. For the purposes of illustration, FIG. 9 shows a perspective view of just the electrodes 812 (without the other parts of the apparatus 801) with a smokable material article 805 inserted therebetween. As in the example above, the combination of the electrodes 812 and the sensing circuitry 813 provides a capacitive sensor. In this example, the sensing circuitry 813 alternates between supplying voltage to one of the capacitor electrodes 812 and allowing voltage to drain from the one of the capacitor electrodes 812. The other of the capacitor electrodes 812 is earthed (for example by being electrically connected to the outer housing 802 of the apparatus 801). The capacitance provided by the electrodes 812, and how that capacitance changes when a smokable material article 805 is received within the housing 802, is monitored so as to enable a determination to be made as to whether or not the smokable material article 805 is "genuine". This may be carried out similarly to the main example described above, i.e. by alternating charging the one of the capacitor electrodes 812 and draining of voltage from the one of the capacitor electrodes 812, both during a calibration phase prior to a smokable material article 805 being received within the housing 802 and then when a smokable material article 805 is received within the housing 802, and counting the number of transitions (from high voltage to low voltage say) that occur in a given time period. Again, however, other methods may be used.

As stated, in this example of FIGS. 8 and 9, the two electrodes 812 are interdigitated. That is, in this example, each electrode 812 is generally annular and has a number of castellations or "fingers" 820 extending generally parallel to the longitudinal axis of the apparatus 801. The electrodes 812 are mounted in the outer housing 802 of the apparatus 801 so that the fingers 820 of one electrode 812 lie between the fingers 820 of the other electrode 820, so as to create a large area of overlap of the electrodes 812 and therefore increase the effective capacitance. In this example, the fit between the fingers 820 of the respective electrodes 812 is a snug fit, though, whilst this is advantageous, a loose (non-contact) fit is also possible.

Figure 10:
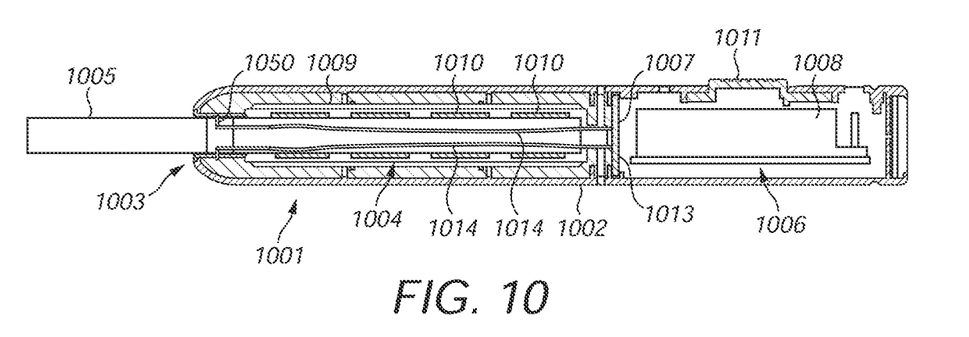
FIG. 10 shows a longitudinal cross-sectional view of another example of an apparatus for heating a smokable material.
Figure 11:
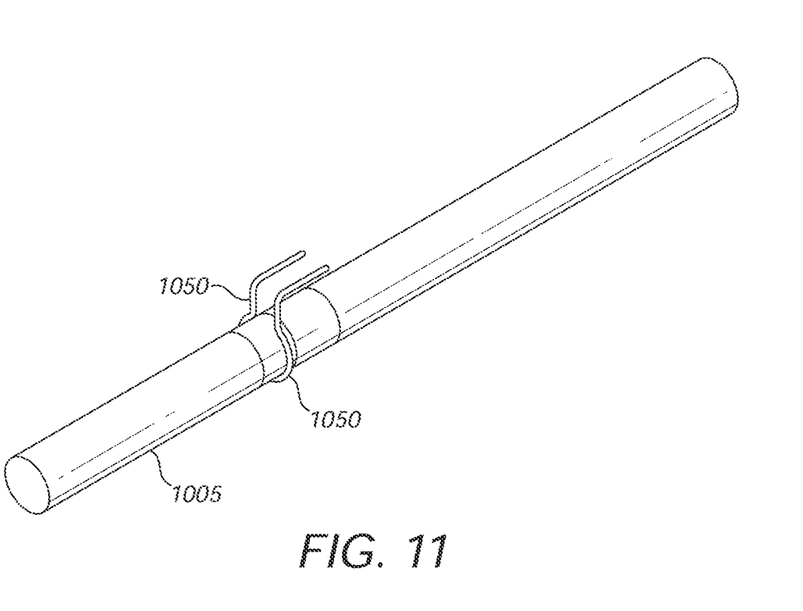
FIG. 11 shows a perspective view of another example of electrodes with a smokable material article inserted therebetween.
Figure 12:
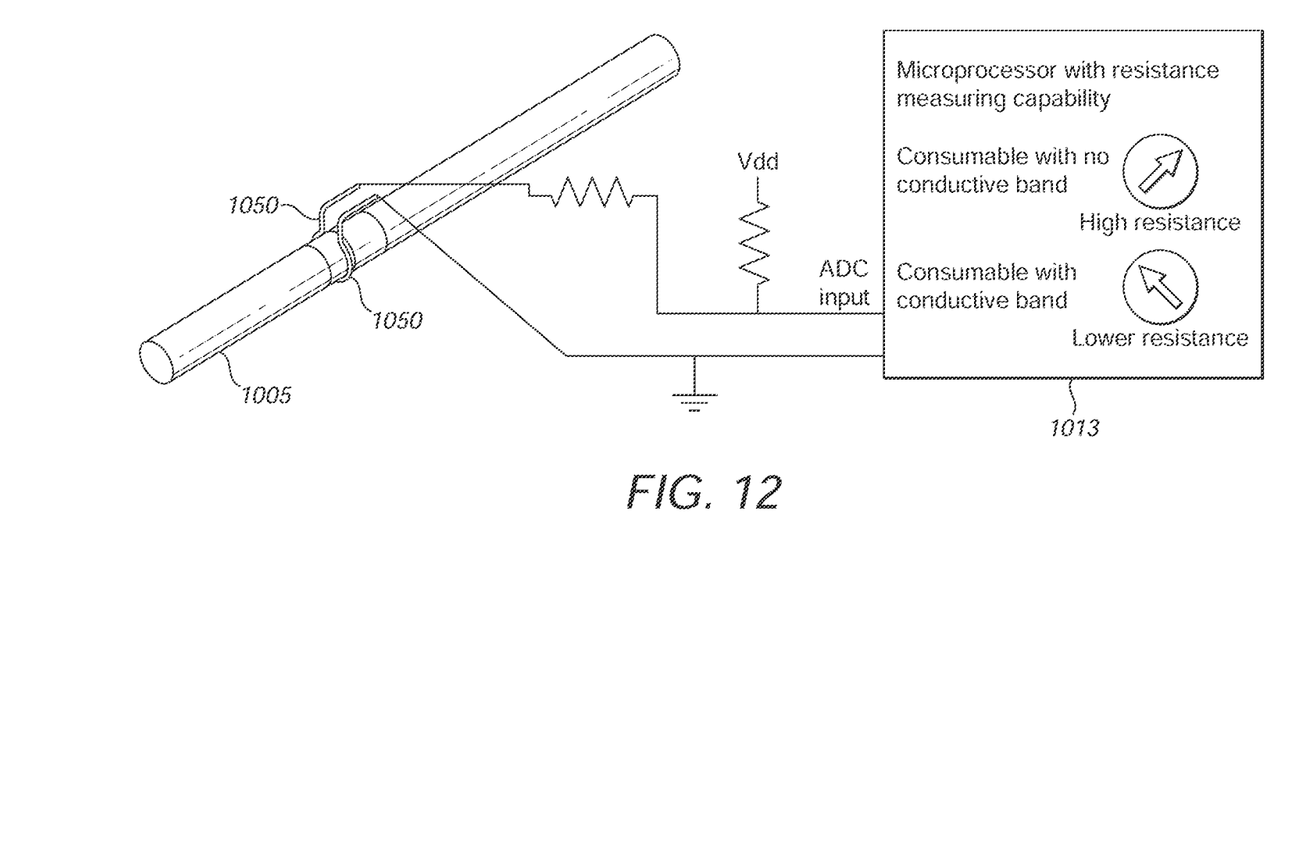
FIG. 12 shows schematically another example of connection of electrodes to sensing circuitry.

FIGS. 10 to 12 show schematically an example of an embodiment in which resistive sensing is used to sense a smokable material article received within the housing. Components and circuitry that are the same as or at least functionally similar to corresponding items in the example of FIGS. 2 and 3 have similar reference numerals, but increased by "1000". Thus, the example apparatus 1001 shown in FIGS. 10 to 12 has an outer housing 1002 having an open end 1003, a heating chamber 1004 which receives a smokable material article 1005 in use, an electronics/power chamber 1006 containing electrical control circuitry 1007 and a power source 1008, a heater support sleeve 1009, plural heating elements or heater segments 1010, and an on/off switch 1011, etc., all of which may be the same as or at least functionally similar to the corresponding components of the example shown schematically in FIGS. 2 to 4. Other heating arrangements are possible, including for example infrared heater segments 1010, which heat by emitting infrared radiation, or resistive heating elements formed by for example a resistive electrical winding around the heater segments 1010. Yet other different heating arrangements may be used.

In the example of FIGS. 10 to 12, the apparatus 1001 has at least two electrically conductive resistance contacts or electrodes 1050 located near the open end 1003 of the outer housing 1002. The two electrodes 1050 are curved, each electrode 1050 being almost semi-circular in cross-section so as to define a generally circular opening into which the smokable material article 1005 passes when received in the housing 1002. The two electrodes 1050 may be formed of a relatively elastic or springy material and may be arranged so as to be biased slightly inwardly, towards each other. This helps to ensure a good physical contact with a smokable material article 1005 when the smokable material article 1005 is introduced into the apparatus 1002.

The electrodes 1050 are connected to sensing circuitry 1013 via connecting wires 1014. The sensing circuitry 1013 may be provided as part of the electrical control circuitry 1007, for example as part of the controller, such as the microprocessor, described above, or as separate circuitry. For the purposes of illustration, FIG. 11 shows a perspective view of just the electrodes 1050 (without the other parts of the apparatus 1001) with a smokable material article 1005 inserted therebetween. The combination of the electrodes 1050 and the sensing circuitry 1013 provides a resistive sensor.

The resistance effectively measured by the electrodes 1050, and how that resistance changes when a smokable material article 1005 is received within the housing 1002, is monitored so as to enable a determination to be made as to whether or not the smokable material article 1005 is "genuine". This may be carried out by for example the electrical control circuitry 1007 causing a reference voltage Vaa to be applied across the electrodes 1050 and detecting the current that is output. A high current indicates that the resistance is low and a small current indicates that the resistance is high. An absolute measure of the resistance may be obtained. Again, however, other methods may be used.

In another example of an embodiment, a combination of capacitive and resistive sensing may be used, using a combination of any of the examples described above. In general, this permits more information about the smokable material article to be obtained. This enables a more precise identification of the smokable material article to be obtained and/or allows more information effectively to be encoded in the smokable material article. In certain embodiments, this also provides for some redundancy in that if for some reason one of the capacitive sensing and the resistive sensing fails, then the other may be used to identify the smokable material article which has been introduced into the apparatus. The capacitive sensing and the resistive sensing may be carried out using the same electrode or electrodes in the apparatus or the capacitive sensing and the resistive sensing may use their own respective dedicated electrode or electrodes.

The electrode or electrodes described above, whether in the form of for example capacitive pads for capacitive sensing or resistive contacts for resistive sensing, are in general electrically conductive. In the case of an electrode or electrodes for capacitive sensing, the electrode or electrodes are preferably mechanically mounted in the body of the apparatus or housing so as to be electrically isolated from the smokable material article when the smokable material article is received in or connected to the apparatus in use. In the case of an electrode or electrodes for resistive sensing, the electrode or electrodes are preferably mechanically mounted in the body of the apparatus or housing so as to make physical contact with the smokable material article when the smokable material article is received in or connected to the apparatus in use. Suitable materials for the electrode or electrodes include copper or copper-containing alloys, including for example a copper foil in the case of capacitive sensing and beryllium-copper in the case of resistive sensing.

Figure 13:
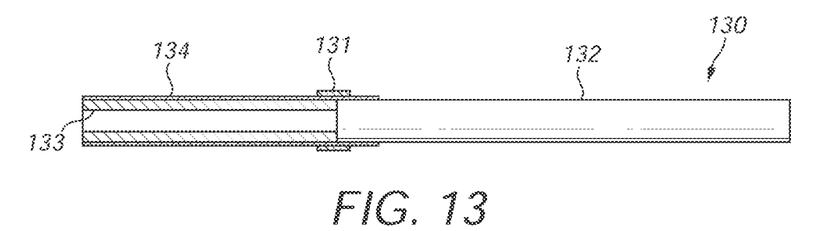
FIG. 13 shows a schematic longitudinal cross-section of an example of a smokable material article.

In FIG. 13, there is shown a schematic longitudinal cross-section of an example of a smokable material article 130 which is provided or formed with some marker or indicium 131, examples of which will be described further below. The smokable material article 130 may be used in conjunction with at least some of the examples of apparatus for heating the smokable material as described herein. The arrangement of the indicium 131 may differ for, and be optimized differently for, the particular heating apparatus.

The smokable material article 130 has a rod 132 of the smokable material. As mentioned above, the smokable material may include for example any tobacco-containing material and may, for example, include one or more of tobacco, tobacco derivatives, expanded tobacco, reconstituted tobacco or tobacco substitutes. "Smokable material" also may include other, non-tobacco, products, which, depending on the product, may or may not contain nicotine. The rod 132 of the smokable material is adjacent an open tube filter 133. The rod 132 and the filter 133 are assembled and held together by being rolled in tipping paper 134 in a manner known per se.

Figure 14:
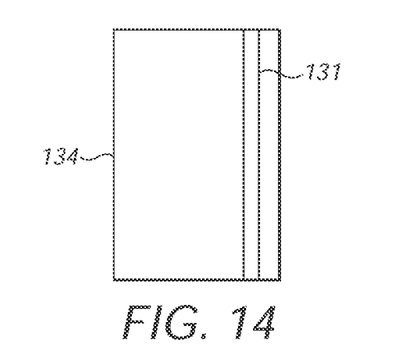
FIG. 14 shows an example of tipping paper.
Figure 15:
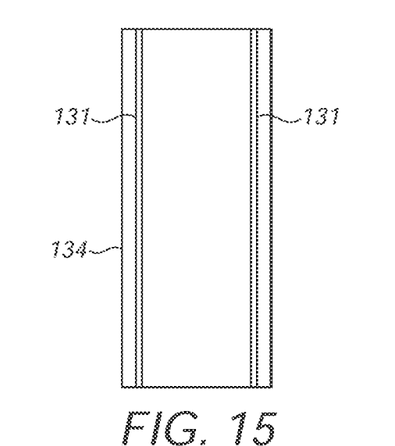
FIG. 15 shows another example of tipping paper.

In the example shown, the marker or indicium 131 is provided on the tipping paper 134. In the example shown, the indicium 131 is in the form of a band of material which, in the assembled smokable material article 130, completely encircles the smokable material article 130. This arrangement facilitates the measuring of the properties of the indicium 131 by the examples of the heating apparatus described above as the particular orientation of the smokable material article 130 within the heating apparatus is not important. Other arrangements are possible. For example, it may not be necessary in all cases for the indicium 131 to completely encircle the smokable material article 130, and instead the indicium 131 may be formed as a different, non-continuous pattern, such as a regular or irregular checkerboard pattern or as a regular or irregular spacing of bands or strips encircling the smokable material article 130. FIG. 14 shows an example of the tipping paper 134 prior to assembly of the smokable material article 130 in which the tipping paper 134 has a single band of the indicium 131. FIG. 15 shows an example of the tipping paper 134 prior to assembly of the smokable material article 130 in which the tipping paper 134 is effectively double width and has a pair of bands of the indicium 131 at opposite edges. During manufacture, the double width tipping paper 134 is cut through the center as pairs of smokable material articles 130 are formed.

To give an idea of scale, in a specific example the rod 132 of the smokable material has a length of around 53 mm, the filter 133 has a length of 30 mm, and the tipping paper may be 35 mm wide (in a direction parallel to the length of the smokable material article 130). The indicium 131 may have a width (again in a direction parallel to the length of the smokable material article 130) of around 4 mm. It is preferred that the thickness of the indicium 131 is small so as not to interfere with the manufacturing process used for the smokable material article or to make it difficult to insert the smokable material article into the heating apparatus. For example, the thickness may be in the approximate range 0.03 mm to 0.3 mm, and more preferably between around 0.03 to 0.05 mm. Indeed, if impregnated into the surface of the smokable material article, the indicium 131 may effectively have no thickness at all. On the other hand, there may be specific applications where a minimum thickness is advantageous in order to enable satisfactory sensing to be achieved.

The marker or indicium 131 may be formed in a number of different ways, and be formed of a number of different materials, depending on the particular sensing arrangement of the heating apparatus with which the smokable material article 130 is intended to be used. The indicium 131 may for example be provided externally of the smokable material article 130, internally of the smokable material article 130, both externally and internally of the smokable material article 130, and/or impregnated into the material of the tipping paper 134. (The indicium 131 is shown in exaggerated form in FIG. 13 for the purposes of illustration.) Where resistive sensing is used (whether on its own or in combination with some other sensing, such as capacitive sensing), the indicium 131 is preferably provided on the outside of the smokable material article 130 so that the resistive sensing electrodes of the heating apparatus can make good electrical contact with the indicium 131. Where capacitive sensing is used, the indicium 131 may be provided internally or externally of the smokable material article 130. The indicium 131 may be provided internally and externally of the smokable material article 130, and/or separate indicia 131 may be provided internally and externally of the smokable material article 130. The marker or indicium 131 may be literally "marked on" the smokable material article 130, such as by printing. Alternatively, the marker or indicium 131 may be provided in or on the smokable material article 130 by other techniques, such as being formed integrally with the smokable material article 130 during manufacture.

In certain examples, and depending on the nature of the sensing that is used to sense and identify the smokable material article 130, the indicium 131 may be formed of an electrically conductive material. The indicium 131 may be for example a conductive ink. The ink may be printed onto the tipping paper 134, using for example a rotogravure printing method, screen printing, ink jet printing, or any other suitable process.

In use, particularly in the context of a heating apparatus that uses a capacitive sensor arranged to sense a change in capacitance when a smokable material article 130 is associated with the heating apparatus, and in particular a heating apparatus that uses (at least) two electrodes which in effect provide the pair of "plates" of a capacitor, the following considerations are relevant. The smokable material article 130, with its electrically conductive indicium or marker 131, creates its own circuit, electrically coupling one sensor electrode with the other. The effectiveness and result of this coupling is affected by the inherent electrical resistance $R_i$ and capacitance C of the smokable material article 130 and/or the indicium 131 in particular. The electrical resistance $R_i$ is in general determined principally by for example the type of ink and formulation chosen for the indicium 131 and by the thickness and width of the indicium 131. Accordingly, the choice of ink for the indicium 131, as well as its application thickness, provide a way of controlling the $R_i$ characteristic over a wide range. The capacitance C is in general determined principally by the axial width of the indicium 131 and the distance of the indicium 131 from the electrodes of the heating apparatus. This distance is in turn determined by the spacing of the electrodes from each other and the thickness (e.g. diameter) of the smokable material article 130. Accordingly, the coupling or "C" characteristic capacitive coupling between the detector electrodes and the indicium 131 on the smokable material article 130 can be determined or controlled through the "fit" of the smokable material article 130 in the heating apparatus, by for example appropriately setting the thickness or diameter of the smokable material article 130 and by controlling the axial widths of the detector electrodes and of the indicium 131.

A particularly suitable material has been found to be a non-metallic conductive ink, that is an ink that is electrically conductive but which contains no metallic materials, or at least contains substantially no metallic materials. The ink may contain carbon for example, which may be in the form of graphite. The ink may therefore be a carbon-based non-metallic electrically conductive ink. The weight resistivity of the ink in a particular example may be in the range approximately 30,000 to 300,000 Ohm-gram/m$^2$. Specific values of the weight resistivity of examples that have been found to be particularly suitable include approximately 38,000 Ohm-gram/m$^2$, 150,000 Ohm-gram/m$^2$ and 290,000 Ohm-gram/m$^2$.

In one particular example, the ink may primarily comprise or consist of a graphite powder and a resin that acts as a binder. The ink may use graphite in an assortment of large and small particle sizes, of which the larger particles form the main path for electrical conduction with the smaller particles "filling in" the gaps between the larger particles. The use of larger sized particles helps to improve electrical conductivity by reducing the number of individual contact points between particles. In another example, the ink may have a crystal structure that uses carbon nano tubes.

It has been found that suitable inks for this purpose include the CI-2001 and CI-2004 conductive carbon inks supplied by Engineered Materials Systems, Inc. of Ohio, USA. These inks are intended for use in printed electronics, such as on printed circuit boards or the like, for example to provide physical and environmental protection at contact areas and to adjust for electrical resistance requirements.

Compared to other techniques, including some techniques known in the prior art, embodiments of the present disclosure have a number of advantages. The sensing arrangements provide a good signal-to-noise ratio, particularly in the case of capacitive sensing. This is of particular benefit in a battery-powered device as less electrical power is consumed in processing the signals and a more accurate determination can be made more quickly. Moreover, as a generality, there will be a manufacturing tolerance during manufacture of smokable material articles such that the outside diameter of the smokable material articles will vary over a range. Such variation may in practice be of the order of 2% to 5% or so for example. In a specific case, the diameter of the smokable material articles may vary from around 5.3 mm to 5.45 mm. Such variations are accommodated well by the present sensing arrangements, including in particular the various capacitive sensing arrangements disclosed herein. This is important as it minimizes the number of "false negatives" that may otherwise occur whereby a genuine smokable material article is inadvertently rejected. The present sensing arrangements may use fewer electrical components, with fewer input/output connections, than some other techniques.

In order to address various issues and advance the art, the entirety of this disclosure shows by way of illustration and example various embodiments in which that which is claimed invention may be practiced and which provide for a superior apparatus arranged to heat but not burn smokable material. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. An apparatus for enabling smokable material to be heated to volatize at least one component of the smokable material, the apparatus comprising:
a housing; and
a resistive sensor arranged to provide a measure of electrical resistance when an article of smokable material has been introduced into the housing in use to enable the article of smokable material to be identified, wherein the resistive sensor comprises one or more electrodes, the one or more electrodes being arranged so as to be biased to provide physical contact with the article of smokable material introduced into the housing.

2. The apparatus according to claim 1, wherein the apparatus comprising a processor constructed and arranged to provide a measure of electrical resistance using the one or more electrodes when the article of smokable material is introduces into the housing in use.

3. The apparatus according to claim 2, wherein the one or more electrodes comprise at least two electrodes, and wherein the at least two electrodes are arranged such that at least a portion of the article of smokable material introduced into the housing in use can be positioned between and in contact with the at least two electrodes, the at least two electrodes in use providing a measure of the electrical resistance of the at least a portion of the article of smokable material.

4. The apparatus according to claim 1, further comprising circuitry constructed and arranged so that the apparatus is only operated to cause heating of the article of smokable material introduced into the housing in use if the electrical resistance meets at least one predetermined criterion.

5. The apparatus according to claim 1, further comprising a heater operable to heat the article of smokable material received within the housing in use.

6. The apparatus according to claim 1, further comprising a sensor arrangement constructed and arranged to identify the article of smokable material when associated with the housing in use by making use of the resistive sensor and at least one other different sensing technique.

7. The apparatus according to claim 6, wherein one of the at least one other different sensing technique uses capacitive sensing.

8. The apparatus according to claim 6, wherein one of the at least one other different sensing technique uses optical sensing.

9. The apparatus according to claim 6, further comprising a heater operable to heat the article of smokable material received within the housing in use.

* * * * *